US011672539B2

(12) United States Patent
Agarwal et al.

(10) Patent No.: US 11,672,539 B2
(45) Date of Patent: *Jun. 13, 2023

(54) VASCULAR COUPLING DEVICE

(71) Applicant: University of Utah Research Foundation, Salt Lake City, UT (US)

(72) Inventors: Jayant P. Agarwal, Salt Lake City, UT (US); Bruce K. Gale, Taylorsville, UT (US); Huizhong Li, Salt Lake City, UT (US); Himanshu J. Sant, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 329 days.

This patent is subject to a terminal disclaimer.

(21) Appl. No.: 16/861,837

(22) Filed: Apr. 29, 2020

(65) Prior Publication Data

US 2020/0253607 A1    Aug. 13, 2020

Related U.S. Application Data

(63) Continuation of application No. 15/108,365, filed as application No. PCT/US2014/071930 on Dec. 22, 2014, now Pat. No. 10,667,816.

(60) Provisional application No. 61/921,324, filed on Dec. 27, 2013.

(51) Int. Cl.
   *A61B 17/11*    (2006.01)
   *A61B 17/00*    (2006.01)

(52) U.S. Cl.
   CPC ..... *A61B 17/11* (2013.01); *A61B 2017/00004* (2013.01); *A61B 2017/1107* (2013.01); *A61B 2017/1132* (2013.01)

(58) Field of Classification Search
   CPC .......... A61B 17/11; A61B 2017/00004; A61B 2017/1107; A61B 2017/1132
   See application file for complete search history.

(56) References Cited

U.S. PATENT DOCUMENTS

| 4,214,586 A * | 7/1980 | Mericle ................. A61M 39/10 606/154 |
| 4,523,592 A | 6/1985 | Daniel |
| 6,030,392 A | 2/2000 | Dakov |
| 6,641,177 B1 * | 11/2003 | Pinciaro .............. F16L 37/0985 285/257 |

(Continued)

FOREIGN PATENT DOCUMENTS

| JP | 55-076649 A | 5/1980 |
| WO | 96/25886 A1 | 8/1996 |

OTHER PUBLICATIONS

US Search International Search Authority, International Search Report and Written Opinion, PCT/US2014/071930.

*Primary Examiner* — Sarah A Simpson
(74) *Attorney, Agent, or Firm* — Workman Nydegger (57) ABSTRACT

Implementations of the present disclosure relate to apparatuses, systems, and methods for anastomosing vascular systems in medical procedures. A pair of similar or identical coupling devices may be disposed at the ends of two vessels, either natural or synthetic. The coupling devices may be capable of hermaphroditically connecting to one another to provide a simple and secure connection which promotes growth of the vessels between the bio-absorbable coupling devices.

18 Claims, 6 Drawing Sheets

(56) References Cited

U.S. PATENT DOCUMENTS

| | | |
|---|---|---|
| 6,666,873 B1 | 12/2003 | Cassell |
| 2001/0029383 A1 | 10/2001 | Solem |
| 2001/0039425 A1 | 11/2001 | Dakov |
| 2004/0116945 A1 | 6/2004 | Sharkawy et al. |
| 2005/0149075 A1 | 7/2005 | Borghi et al. |
| 2013/0110140 A1 | 5/2013 | Lin et al. |

* cited by examiner

VASCULAR COUPLING DEVICE

CROSS-REFERENCE TO RELATED APPLICATIONS

This application is a continuation of U.S. patent application Ser. No. 15/108,365, filed Jun. 27, 2016 and titled "Vascular Coupling Device", which is a 35 U.S.C. § 371 filing of International Application No. PCT/US2014/071930, filed Dec. 22, 2014 and titled "Vascular Coupling Device", which claims priority to and the benefit of U.S. Provisional Patent Application No. 61/921,324, filed Dec. 27, 2013 and titled entitled "Vascular Coupling Device", the entireties of each of the foregoing being incorporated herein by this reference.

BACKGROUND

1. The Field of the Disclosure

Generally, this disclosure relates to surgical anastomosis. More specifically, the present disclosure relates to devices, systems, methods that related to the mechanical coupling of vasculature, natural or synthetic, in a medical setting.

2. Background and Relevant Art

Anastomosis is the connection of the vessels within a body. While it may refer generally to conduits within a body, anastomosis as used herein may refer to circulatory anastomosis, in which vascular tissue may be connected or reconnected. The circulatory system is very complex and its proper function is critical to a patient's health and wellbeing. However, a surgeon may need to bypass or modify a patient's circulatory system to provide proper therapeutic treatments.

Unfortunately, the vasculature of a patient consists of small conduits that can be difficult to handle and manipulate properly, even when considered independent of the small incisions, bodily fluids present, and other complicating factors that commonly occurring during procedures in an operating room. Blood vessels may be relatively small and difficult to handle properly in order to perform common methods of connecting tissue, such as suturing. Furthermore, the small structures of the vasculature may not be suitable for other connection methods, such as surgical staples, as the staples would damage the walls of the blood vessel or constrict flow therethrough.

Conventional microsurgical vessel anastomosis is hand suturing the two cut ends of an artery or vein together using ultrafine techniques with the assistance of an operating microscope. This technique requires specialized training, is time consuming, is expensive when considering doctor and operating room time, and is subject to a great degree of human error.

SUMMARY

Implementations of the present disclosure solve one or more of the foregoing or other problems in the art with apparatuses, systems, and methods for surgical anastomosis.

In an embodiment, a vascular coupling device for providing a coupling site on a vessel may comprise a back ring configured to slide around the vessel. An engaging coupler, with an inner surface having a diameter greater than a diameter of an outer diameter of the back ring, may be disposed around the back ring. An end of the vessel may be everted over the outer surface of the back ring and compressed between the inner surface of the engaging coupler and the outer surface of the back ring. The vascular coupling device may further comprise a plurality of engaging arms extending longitudinally from an outer surface of the engaging coupler. The engaging arms may have a length sufficient to reach around a second coupling device and engage a back ring of a second coupling device.

A vascular coupling system for coupling a first vessel to a second vessel is also presented. The system may comprise a first coupling device and a second coupling device. The first and second coupling device may each comprise a back ring and an engaging coupler as previously described. The first coupling device and second coupling device may further be identical. The first and second coupling devices may be configured to hermaphroditically engage one another. In an embodiment, the first and second coupling devices may engage one another when oriented at a rotational offset from one another.

A method for coupling a first vessel to a second vessel is also presented herein. In an embodiment, the method may comprise positioning a first back ring circumferentially around an end of the first vessel and everting the end of the first vessel over an outer diameter of the first back ring. The method may further comprise assembling a first coupling device by sliding an inner surface of a first engaging coupler over the end of the first vessel and an outer surface of the first back ring. Sliding the inner surface of the first engaging coupler over the end of the first vessel and an outer surface of the first back ring may create a friction fit of the first engaging coupler and the first back ring with the end of the first vessel disposed therebetween that is substantially sealed. The method may further comprise engaging the first coupling device with a second coupling device, wherein a plurality of engaging arms extending from the first engaging coupler fit within a recessed portion of the second coupling device.

Additional features and advantages of exemplary implementations of the disclosure will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. For better understanding, the like elements have been designated by like reference numbers throughout the various accompanying figures. While some of the drawings may be schematic, it should be understood that at least part of drawings may be drawn to scale. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

One or more implementations of the present disclosure relate to assembling and installing vascular coupling devices that are secured to a blood vessel and couple to one another. The vascular coupling devices may secure to the end of the vessel without piercing or puncturing the vessel wall. The vascular coupling device may then secure to another vascular coupling device simply and reliably, providing a bio-absorbable connection that is easy to install.

A vascular coupling device may have two parts that combine via a friction fit to simultaneously form the vascular coupling device and to reliably retain the end of the vessel relative to the vascular coupling device. A user may pass the end of a vessel through the annular back ring and then evert the end of the vessel outward and over the outer surface of the back ring. A user may then slide the engaging coupler over the outer surface of the back ring and the everted vessel now laid thereupon. Pressing the engaging coupler may create a substantially watertight (i.e., fluid tight) friction fit such that the vessel now terminates in the coupling device. A user may then affix a similar vascular coupling device on a second vessel. The two vascular coupling devices may each be able to mutually engaged one another to provide a secure connection wherein the vessel walls are urged against one another to promote vessel growth.

Figure 1A:
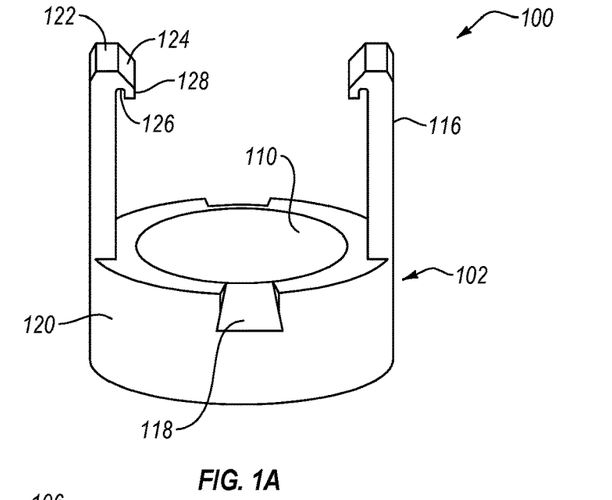
FIGS. 1A-B are perspective views of components of a vascular coupling device, according to at least one embodiment of the present disclosure.
Figure 1B:
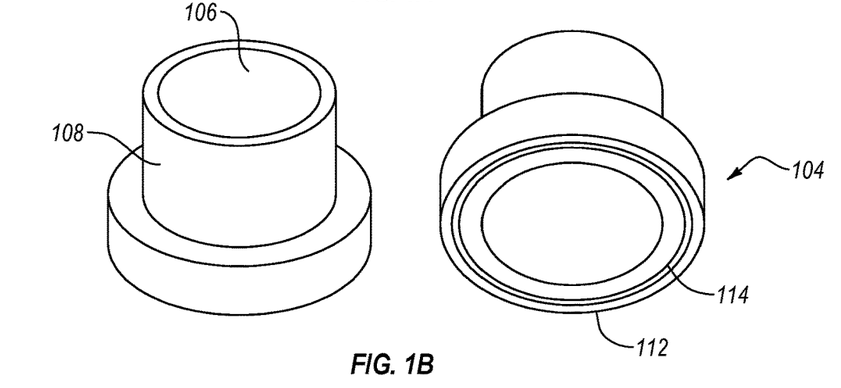

FIG. 1A shows an engaging coupler 102 and FIG. 1B depicts a top perspective and bottom perspective of a back ring 104, which may collective form a vascular coupling device 100. In an embodiment, the engaging coupler 102 and the back ring 104 may comprise a bio-absorbable or bio-compatible material. For instance, exemplary bio-compatible materials may include organic materials, metals, alloys, polymers, composites, and combinations thereof. According to at least one example, the engaging coupler 102 and the back ring 104 may be made from a biocompatible material such as silicone, high density polyethylene ("HDPE"), polymethyl methacrylate ("PMMA"), or combinations thereof. In other embodiments, biocompatible materials such as titanium, cobalt, platinum, nickel, stainless steel, other materials, alloys thereof, or combinations of the foregoing may also be utilized. The engaging coupler 102 and the back ring 104 may be designed to remain in the body indefinitely, or may degrade over time. For instance, the engaging coupler 102 and the back ring 104 may be formed of a biodegradable, bioerodable, bioresorbable, or other degrading or resorbing material or combinations thereof. Examples of such materials that may be suitable for the manufacture of the device may include, but are not limited to, poly(lactic-co-glycolic acid) ("PLGA"), collagen, spun silk, electrospun silk, polytetrafluoroethylene ("PTFE"), polydimethylsiloxane ("PDMS"), silicone, a salicylic acid-based polymer, a salicylsalicylic acid-based polymer, a difluorophenyl-salicylic acid-based polymer, collagen, fibrin, fibronectin, alginate, poly-glycolic acid, poly-(lactic acid), poly-caprolactone, poly-(L-lactic acid), poly(3-hydroxybutyric acid), poly((bis(hydroxyethy) terephthalate-ethyl phosphoester/terephthaloyl chloride), gelatin, keratin, thrombin, poly(2-hydroxyethyl methacrylate) ("PHEMA"), a co-polymer of PHEMA and methyl methacrylate, poly (acrylonitrile-co-methylacrylate), or combinations thereof.

The back ring 104 may have an inner surface 106 that is smooth. The smooth inner surface 106 of the back ring 104 may help prevent damage to the vessel wall during anastomosis. The back ring 104 may also have an outer surface 108. The outer surface 108 may have a constant radius, or may taper slightly, such that the top portion of the outer surface 108 has a smaller radius than the bottom portion of the outer surface 108. A tapered outer surface 108 may assist in forming a friction fit with an inner surface 110 of a body of the engaging coupler 102. The back ring 104 may also have a rear face 112 with a circular groove 114 disposed therein. The circular groove 114 provides a recessed portion of the rear face 112 with which a second vascular coupling device may engage.

The engaging coupler 102 may have various shapes. In some embodiments, the engaging coupler 102 may be an engaging ring with a body having an annular structure. In other embodiments, the engaging coupler 102 may be elliptical, polygonal, irregularly shaped, or combinations thereof. The inner surface 110 of the body of the engaging coupler 102 may be configured to complimentarily mate with the outer surface 108 of the back ring 104. In yet other embodiments, the engaging coupler 102 may not surround the entire outer surface 108 of the back ring 104. For example, the engaging coupler 102 may have a body with an opening or break allowing the engaging coupler 102 to expand and/or contract radially and clip around at least a portion of the back ring 104.

The engaging coupler 102 may comprise at least one resilient engaging arm 116. While FIG. 1A depicts an embodiment of the engaging coupler 102 with two engaging arms 116, other numbers of engaging arms 116 are possible, and in other embodiments, the engaging coupler 102 may have one, three, four, or more engaging arms 116. The engaging arms 116 may extend longitudinally from the body of the engaging coupler 102 and be disposed around the circumference of the engaging coupler 102. In an embodiment, the engaging arms 116 are disposed at equal angular displacements. For example, when the engaging coupler 102 comprises two engaging arms 116, the engaging arms may be disposed at about 180° intervals. In another example, when the engaging coupler 102 comprises three engaging arms 116, the engaging arms may be disposed at about 120° intervals. However, in another embodiment, the engaging arms 116 may be disposed at unequal intervals. For example, when the engaging coupler 102 comprises two engaging arms 116, the engaging arms 116 may be disposed at about a 90° interval and about a 270° interval.

The engaging coupler 102 may also comprise a plurality of cuts 118 in an outer surface 120 of the engaging coupler 102. While FIG. 1A depicts an embodiment of the engaging coupler 102 with two cuts 118, other numbers of cuts 118 are possible, and in other embodiments, the engaging coupler may have three or four cuts 118. In an embodiment, the cuts 118 are disposed at equal angular displacements. For example, when the engaging coupler 102 comprises two cuts 118, the engaging arms may be disposed at about 180° intervals. In another example, when the engaging coupler 102 comprises three cuts 118, the engaging arms 116 may be disposed at 120° intervals. However, in another embodiment, the cuts 118 may be disposed at unequal intervals. For example, when the engaging coupler 102 comprises two cuts 118, the cuts 118 may be disposed at about a 90° interval and about a 270° interval. In another example, there may be more or fewer cuts 118 than there are engaging arms 116 (e.g., one cut 118 per two engaging arms 116 or two cuts 118 per one engaging arm 116).

Figure 2:
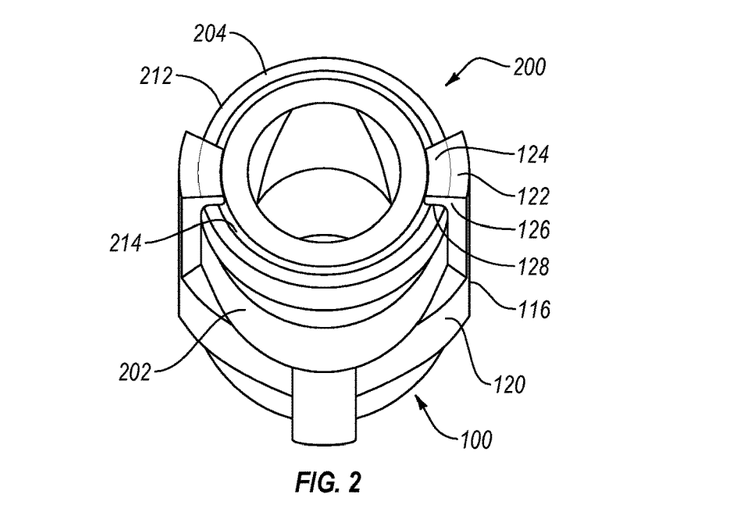
FIG. 2 is a perspective view of two vascular coupling devices in accordance with the present disclosure engaged and forming a fluid connection.

As shown in FIG. 2, the engaging arms 116 may further comprise engaging features to engage with a second vascular coupling device 200. The engaging features of the first vascular coupling device 100 may include a hook 122 with a beveled face 124 and undercut groove 126 with an associated tab 128. In some embodiments, the engaging arms 116 may have a length sufficient to extend beyond the rear face 112 of a second vascular coupling device 200. When the engaging arms 116 extend beyond the rear face 112 of the second vascular coupling device 200, the hooks 122 on the engaging arms 116 may extend laterally and contact the rear face 112. Furthermore, the undercut groove 126 and associated tab 128 may interface with the circular groove 114 on the rear face 112 of the second vascular coupling device 200. In other embodiments, other engaging features may be used. For example, the engaging features may include threads for engaging a threaded portion of the second vascular coupling device 200. In another example, the engaging features may include a snap fit ramp that may be inserted into a corresponding slot in the second vascular coupling device 200. Furthermore, in some embodiments the engaging features may vary depending on the engaging arm 116. In yet other examples, the engaging feature may be one or more features (e.g., a coating or surface texture) to enhance or facilitate the frictional force between the engaging coupler 102 and the back ring 104.

As can be seen in FIG. 2, the first vascular coupling device 100 and second vascular coupling device 200 may mutually engage when coupled. In at least one embodiment, the first vascular coupling device 100 and second vascular coupling device 200 may be identical in structure, and the connection therebetween may be hermaphroditic. In other embodiments, the first vascular coupling device 100 and second vascular coupling device 200 may not be identical although the connection therebetween may be hermaphroditic. In the embodiment depicted in FIG. 2, the first vascular coupling device 100 and second vascular coupling device 200 are identical embodiments having two engaging arms 116 and two cuts 118 in each coupling device. The first and second vascular coupling devices 100, 200, have engaging arms 116 disposed about 180° from one another and cuts 118 disposed about 180° from one another and about 90° from either of the engaging arms 116. The cuts 118 may interact with the beveled faces 124 of the hooks 122 on the engaging arms 116 to urge the resilient engaging arms 116 radially outward and around the outer surface 120 of the engaging coupler 102. Therefore, to ensure proper alignment of the cuts 118 and the beveled faces 124 of the hooks 122 on the engaging arms 116, the first vascular coupling device 100 and second vascular coupling device 200 may be oriented with about a 90° rotational offset from one another prior to coupling. To aid in preventing subsequent rotation of the first vascular coupling device 100 and second vascular coupling device 200 relative to one another, the outer surface 120 of the engaging coupler 102 may be non-circular, such as elliptical, with the engaging arms 116 disposed at a major axis and the cuts 118 disposed at a minor axis of the ellipse.

Figure 3A:
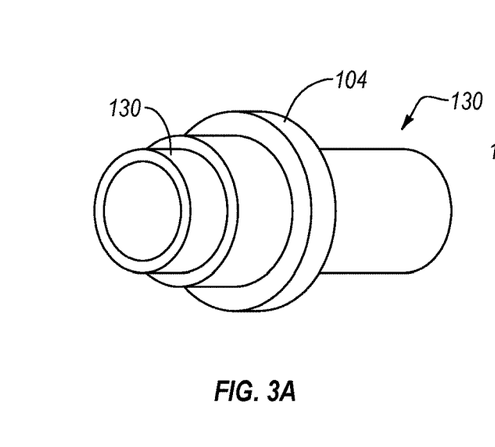
FIGS. 3A-E are perspective views of the installation and coupling of the two vascular coupling devices of FIG. 2.
Figure 3B:
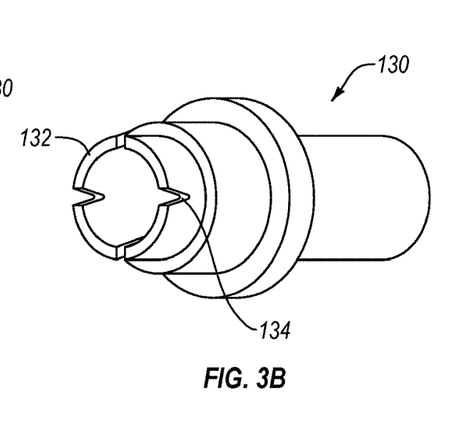

A method for anastomosing is also described herein and depicted in FIGS. 3A-E. The method may comprise sliding a back ring 104 around a vessel 130 (FIG. 3A). In an embodiment, approximately 2 mm to approximately 3 mm of the vessel protrudes from the back ring 104. In some embodiments, the back ring may be fixedly attached to the engaging coupler 102. For example, as will be described below, a proximally extending engaging arm may limit proximal movement of the back ring. The protruding end 132 of the vessel 130 may then have one or more slits 134 cut approximately one-half to approximately two-thirds of the distance to the back ring 104 (FIG. 3B). In the aforementioned embodiment, the one or more slits 134 may extend about 1 mm to about 2 mm longitudinally into the vessel 130.

The protruding end 132 of the vessel 130 may be everted over the outer surface 108 of the back ring 104. An engaging coupler 102 may then be slid onto the outer surface 108 of the back ring 104 and may compresses the everted protruding end 132 of the vessel 130 to secure the first vascular coupling device 100 on the end of the vessel 130 (FIG. 3C).

Figure 3C:
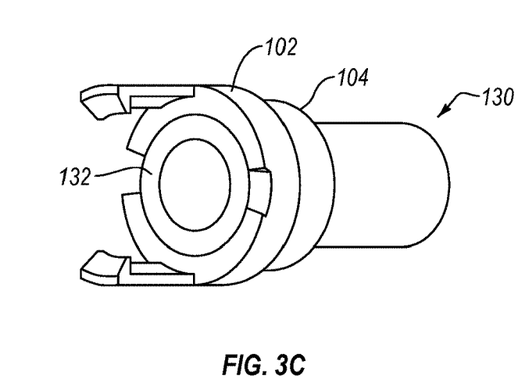
Figure 3D:
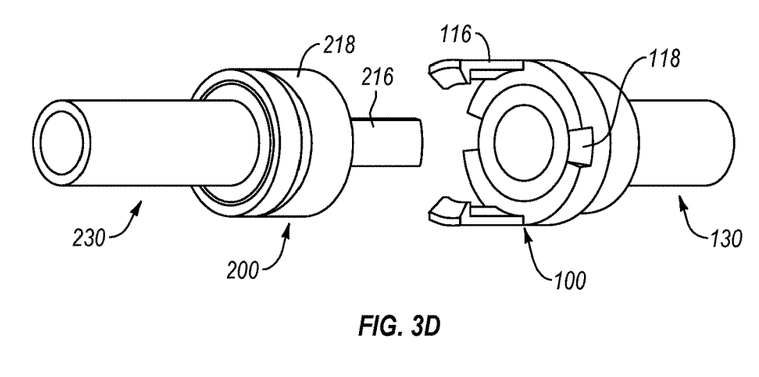

The acts depicted in FIGS. 3A through 3C may be repeated to secure a second vascular coupling device 200 to a second vessel 230. The first vascular coupling device 100 and the second vascular coupling device 200 may then be oriented with a rotational offset from one another to align the engaging arms 116 of first vascular coupling device 100 with the cuts 218 of the second vascular coupling device 200 (FIG. 3D) and the engaging arms 216 of the second vascular coupling device 200 with the cuts 118 of the first vascular coupling device 100. In the depicted embodiment, the offset is about 90°, but in embodiments with other numbers of engaging arms 116, 216, the offset may be about 60°, about 45°, or other angles.

Figure 3E:
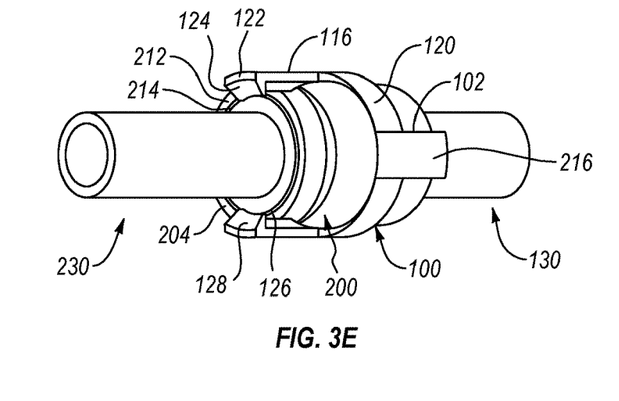

The first vascular coupling device 100 and the second vascular coupling device 200 may then be moved toward one another. The beveled faces 124 of the hooks 122 on the engaging arms 116 of the first vascular coupling device 100 may interact with the cuts and urge the resilient engaging arms 116 outward and around the outer surface 220 of the engaging coupler 202 of the second vascular coupling device 200. When the first vascular coupling device 100 and the second vascular coupling device 200 meet, the first vessel 130 and the second vessel 230 may contact one another. Additionally, the hooks 122 on the engaging arms 116 of the first vascular coupling device 100 may extend radially inward and contact a back ring 204 of the second vascular coupling device 200. Furthermore, the undercut groove 126 and associated tab 128 of the hooks 122 on the engaging arms 116 of the first vascular coupling device 100 may interface with the rear face 212 and circular groove 214 of the second vascular coupling device 200, securing the first vascular coupling device 100 to the second vascular coupling device 200 (FIG. 3E).

Figure 4:
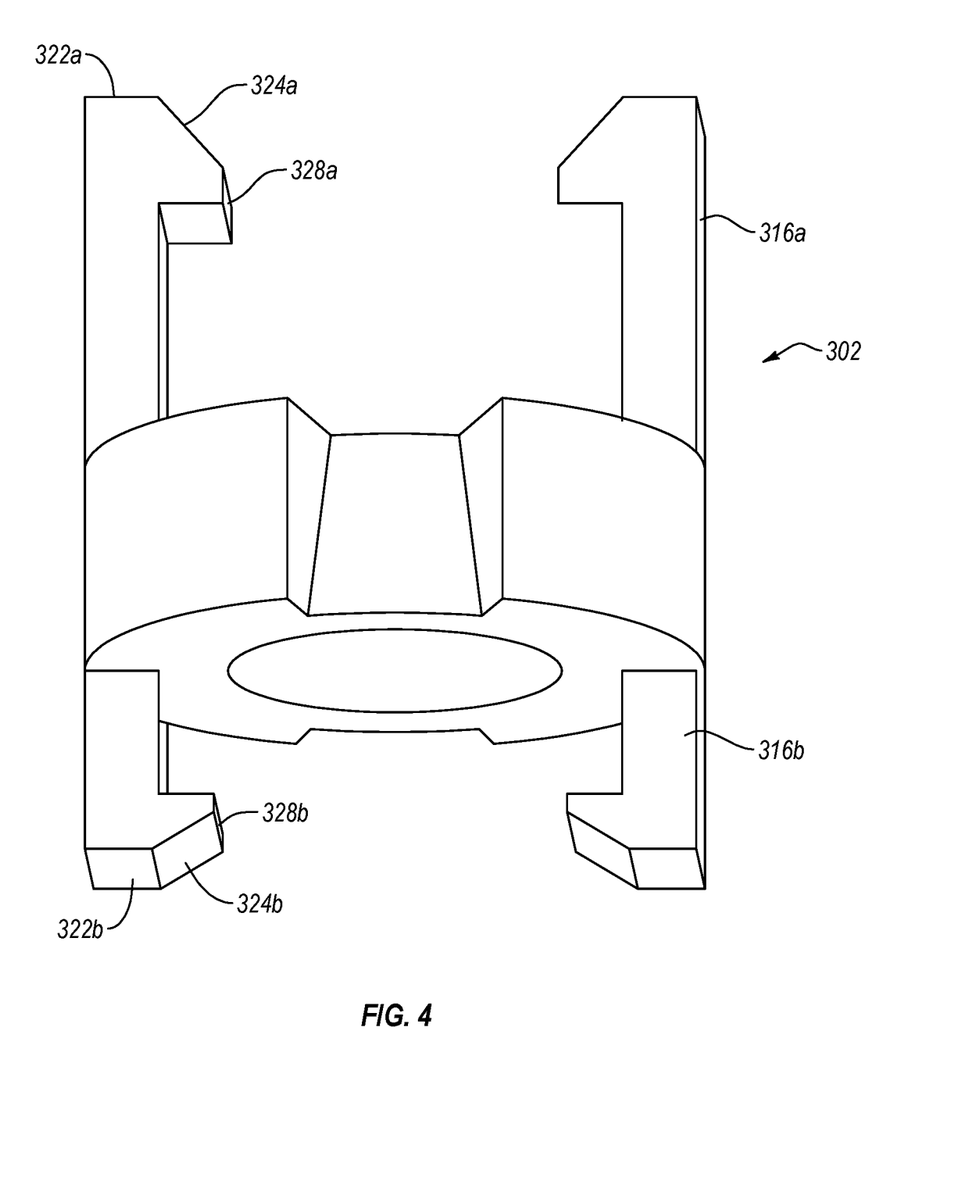
FIG. 4 is a perspective view of another embodiment of an engaging coupler having proximal engaging arms
Figure 5:
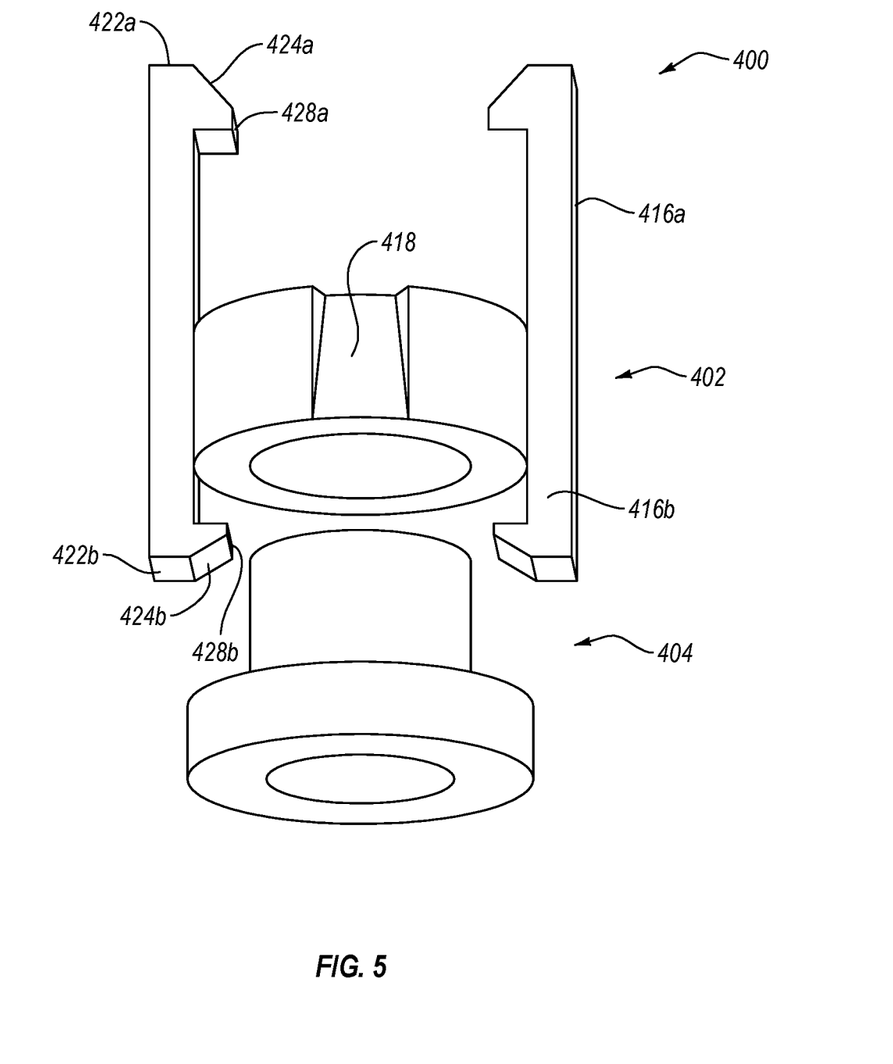
FIG. 5 is a perspective view of a vascular coupling device having a back ring and an engaging coupler including proximal engaging arms.

FIG. 4 shows an alternative embodiment of an engaging coupler 302 and FIG. 5 depicts a bottom perspective exploded view of yet another embodiment of an engaging coupler 402 and an alternative embodiment of a back ring 404. The embodiments shown in FIGS. 4-6 may include any or all of the components of the embodiments shown and/or described in connection with FIGS. 1-3E. Thus, the various alternatives presented in the alternative embodiments shown and/or described in connection with FIGS. 4-6 may be combined with any of the various alternatives presented in the alternative embodiments shown and/or described in connection with FIGS. 1-3E. Similar components may be identified by like numbers.

In the illustrated embodiment, the engaging coupler 302 and the back ring 304 may comprise a bio-absorbable or bio-compatible material as described herein. The back ring 304 may have an inner surface 306 and an outer surface 308. The back ring 304 may also have a rear face 312.

Figure 6:
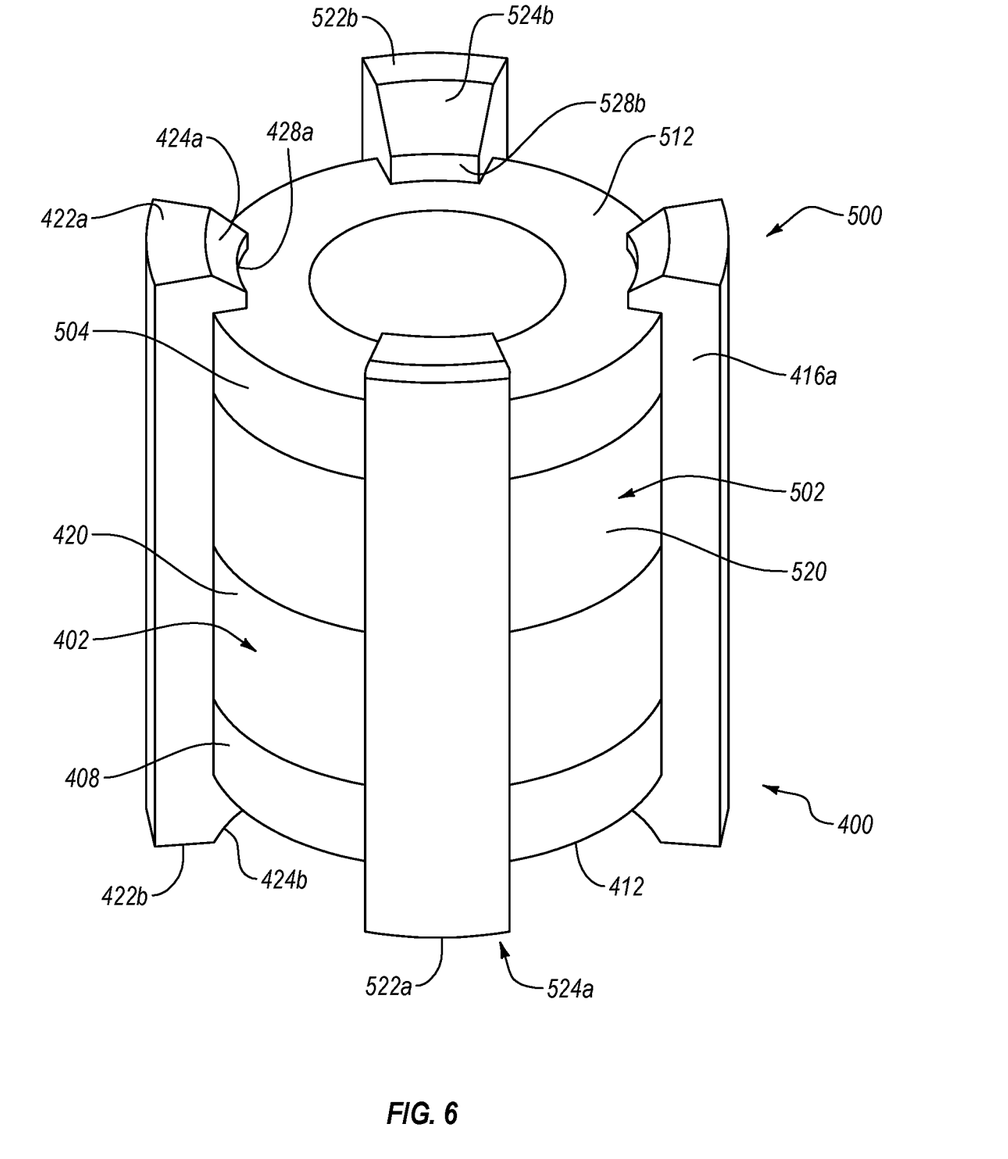
FIG. 6 is a perspective view of alternative embodiments of two vascular coupling devices in accordance with the present disclosure engaged and forming a fluid connection.

The engaging coupler 302 may comprise at least one resilient distally extending engaging arm ("distal engaging arm") 316a. While FIG. 4 depicts an embodiment of the engaging coupler 302 with two distal engaging arms 316a, other numbers of distal engaging arms 316a are possible, and in other embodiments, the engaging coupler 302 may have one, three, four, or more distal engaging arms 316a. The engaging coupler 302 may comprise at least one proximally extending engaging arm ("proximal engaging arm") 316b. Although shown with two proximal engaging arms 316b, more or fewer proximal engaging arms 316b may be used. Additionally, as with the embodiment of an engaging coupler 302 shown in FIGS. 4-6, the embodiment of an engaging coupler 102 shown in FIGS. 1-3E may include any number of engaging arms (i.e., 0, 1, 2, 3, 4 or more), which may extend distally (such as engaging arms 116 or 316a) and/or proximally (such as engaging arms 316b). The engaging arms 316a, 316b may extend longitudinally from the annular engaging coupler 302 and be disposed around the circumference of the engaging coupler 302. In an embodiment, the engaging arms 316a, 316b are disposed at equal angular displacements and/or unequal intervals. Furthermore, the distal engaging arms 316a and the proximal engaging arms 316b may be circumferentially aligned (as shown in FIGS. 4-6), circumferentially misaligned, otherwise aligned, or combinations thereof.

In some embodiments, the proximal engaging arms 316b may engage with a back ring by a friction force (e.g., an interference fit) with a surface of the back ring. In other embodiments, the proximal engaging arms 316b may have engaging features similar to the distal engaging arms 316a or different from the distal engaging arms 316a. For example, the distal engaging arms 316a may have engaging features including hooks 322a with a beveled face 324a and a tab 328a. In some embodiments, the proximal engaging arms 316b may have engaging features including hooks 322b with a beveled face 324b and a tab 328b. The engaging features of the proximal engaging arms 316b may be configured to engage with a back ring.

FIG. 5 illustrates vascular coupling device 400 including an engaging coupler 402 having proximal engaging arms 416b similar to or the same as engaging arms 316b described in relation to FIG. 4. The proximal engaging arms 416b may interact with a back ring 404. For example, the proximal engaging arms 416b may include engaging features such as a hook 422a with a beveled face 424a and an associated tab 428a. The proximal engaging arms 416b may limit proximal motion of the back ring 404 when the engaging coupler 402 is engaged with the back ring 404 prior to and/or during engagement with a second vascular coupling device.

The engaging coupler 402 may also comprise a plurality of cuts 418 in an outer surface 420 of the engaging coupler 402. The engaging coupler 402 may not include any cuts or may include any number of cuts 418. The number of cuts 418 may or may not correspond to a number of engaging arms (i.e., 116, 416) in a second vascular coupling device. The cuts 418 may be disposed at equal or unequal angular displacements.

The engaging arms 416 may further comprise engaging features to engage with a second vascular coupling device. The engaging features may include a hook 422a with a beveled face 424a and an associated tab 428a. As can be seen in FIG. 6, in an embodiment, the distal engaging arms 416a may have a length sufficient to extend beyond the rear face 512 of a second vascular coupling device 500. When the distal engaging arms 416a extend beyond the rear face 512 of the back ring 504 of the second vascular coupling device 500, the hooks 422a on the distal engaging arms 416a may extend laterally and contact the rear face 512. In other embodiments, other engaging features may be used.

As can be seen in FIG. 6, the first vascular coupling device 400 and the second vascular coupling device 500 may mutually engage when coupled. In an embodiment, the first vascular coupling device 400 and second vascular coupling device 500 may be similar or identical in structure, and the connection therebetween may be hermaphroditic. In other embodiments, the first vascular coupling device 400 and second vascular coupling device 500 may not be identical although the connection therebetween may be hermaphroditic. In the embodiment depicted in FIG. 6, the first vascular coupling device 400 and second vascular coupling device 500 are identical embodiments having two pluralities of distal engaging arms 416a, 516a and two pluralities of proximal engaging arms 416b, 516b and two cuts (not shown) in each coupling device. The first and second coupling devices 400, 500, have engaging arms 416a, 516a, 416b, 516b disposed about 180° from one another and cuts 418 disposed about 180° from one another. The first vascular coupling device 400 and second vascular coupling device 500 may be rotated about 90° relative to one another.

A plurality of cuts may interact with the beveled faces 424, 524 of the hooks 422, 522 on the distal engaging arms 416a, 516a of the first vascular coupling device 400 and the second vascular coupling device 500, respectively, to urge the resilient distal engaging arms 416a, 516a radially outward and around the outer surface 420, 520 of the engaging couplers 402, 502. Therefore, to ensure proper alignment of the cuts and the beveled faces 424, 524 of the hooks 422, 522 on the engaging arms 416a, 516a, the first vascular coupling device 400 and second vascular coupling device 500 may be oriented with about a 90° rotational offset from one another prior to coupling. To aid in preventing subsequent rotation of the first vascular coupling device 400 and second vascular coupling device 500 relative to one another, the outer surface 420, 520 of the engaging coupler 402, 502 may be elliptical, with the distal engaging arms 416a, 516a disposed at a major axis and the cuts disposed at a minor axis of the ellipse.

Figure 7A:
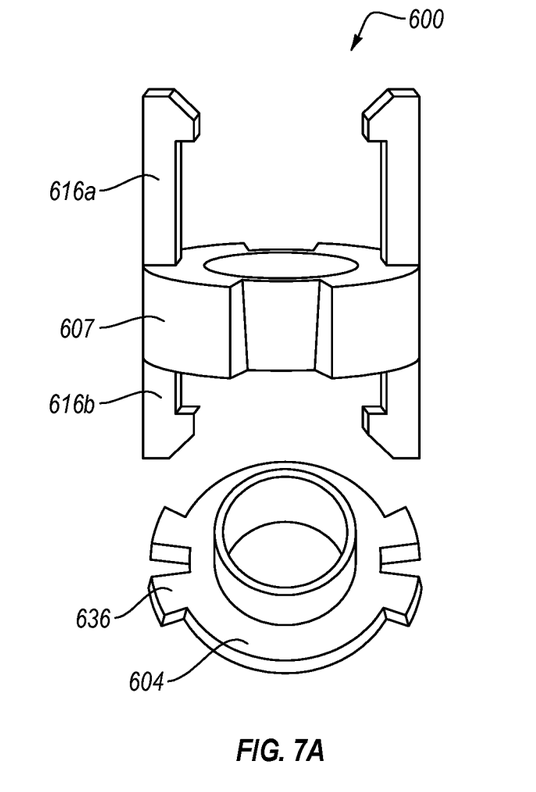
FIGS. 7A-B depict yet another embodiment of a vascular coupling
Figure 7B:
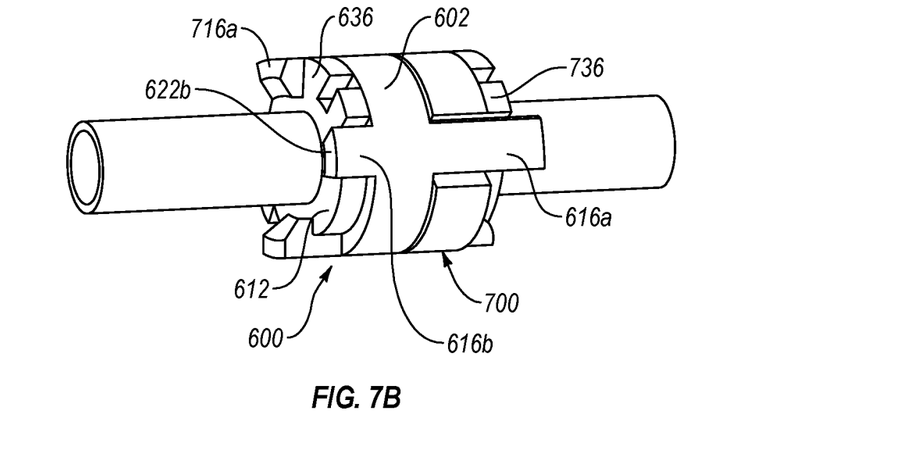

FIGS. 7A-B illustrate yet another embodiment of a vascular coupling device 600 including at least one feature to limit the rotational movement of a first vascular coupling device relative to a second vascular coupling device. FIG. 7A is an exploded view of yet another embodiment of a vascular coupling device 600 having and engaging coupler 602 and a back ring 604. The engaging coupler 602 may include a plurality of distal engaging arms 616a and proximal engaging arms 616b. The proximal engaging arms 616b may be configured to engage with and limit the movement of a back ring 604. The back ring 604 may include one or more lateral extensions 636. The lateral extensions 636 may allow the back ring 604 to have an outer diameter at the lateral extensions 636 that is greater than an inner diameter defined by the plurality of distal engaging arms 616a and/or proximal engaging arms 616b. For example, the distal engaging arms 616a and/or proximal engaging arms 616b may define a distance therebetween larger than at least a portion of the back ring 604 but smaller than another portion of the back ring 604 including the lateral extensions 636.

FIG. 7B illustrates a first vascular coupling device 600 and a second vascular coupling device 700 coupled together. The engaging coupler 602 and back ring 604 of the first vascular coupling device 600 are coupled together with a plurality of engaging features (i.e., hooks 622b) on the proximal engaging arms 616b in contact with a rear face 612 of the back ring 604. In some embodiments, the back ring 604 and engaging coupler 602 may be rotatable relative to one another when engaged. In other embodiments, rotational movement of the back ring 604 and the engaging coupler 602 may be limited or prevented when engaged. For example, the rotational movement of the back ring 604 and the engaging coupler 602 may be limited or prevented by friction, an adhesive, a mechanical fastener, or by physical contact between a portion of the engaging coupler 602 and the back ring 604. The proximal engaging arms 616b may contact the rear face 612 of the back ring 604. At least one proximal engaging arm 616b may contact or be adjacent to at least one lateral extension 636 when the engaging coupler 602 and back ring 604 are rotated relative to one another. The contact of the proximal engaging arms 616b and the lateral extensions 636 may limit or prevent the rotation of the engaging coupler 602 and back ring 604 are rotated relative to one another.

As described herein, the first vascular coupling device 600 and second vascular coupling device 700 may be oriented at an angle (e.g., a rotational angle) relative to one another. The rotational offset of the first vascular coupling device 600 and second vascular coupling device 700 may have a rotational gap between the distal engaging arms 616a of the first vascular coupling device 600 and the distal engaging arms 716a of the second vascular coupling device 700. The rotational gap between the distal engaging arms 616a of the first vascular coupling device 600 and the distal engaging arms 716a of the second vascular coupling device 700 may be within a range having upper and lower values including any of 5°, 10°, 15°, 20°, 25°, 30°, 35°, 40°, 45°, 50°, 55°, 60°, 65°, 70°, 75°, 80°, 85°, or any value therebetween. For example, the rotational gap may be between 30° and 75°. In another example, the rotational gap may be between 45° and 65°.

In some embodiments, the lateral extension 636 of the first vascular coupling device 600 and/or a lateral extension 736 of the second vascular coupling device 700 may be configured to occupy a portion of the rotational gap and limit rotational movement of the first vascular coupling device 600 and second vascular coupling device 700 relative to one another. The lateral extension 636 of the first vascular coupling device 600 and/or the lateral extension 736 of the second vascular coupling device 700 may be configured to occupy a percentage of the rotational gap having upper and lower values including any of 10%, 15%, 20%, 25%, 30%, 35%, 40%, 45%, 50%, 55%, 60%, 65%, 70%, 75%, 80%, 85%, 90%, 95%, or any value therebetween. For example, the lateral extension 636 of the first vascular coupling device 600 and/or the lateral extension 736 of the second vascular coupling device 700 may occupy a percentage of the rotational gap between 50% and 95%. In another example, the lateral extension 636 of the first vascular coupling device 600 and/or the lateral extension 736 of the second vascular coupling device 700 may occupy a percentage of the rotational gap between 60% and 90%. In yet another example, the lateral extension 636 of the first vascular coupling device 600 and/or the lateral extension 736 of the second vascular coupling device 700 may occupy a percentage of the rotational gap between 80% and 90%.

A vascular coupling device or system of a plurality of vascular coupling devices according to the present disclosure may allow the fluid communication between a first vessel and second vessel. The first vessel and second vessel may be contact with one another to facilitate intergrowth and healing of the vessel without further damage to or interference with the vessel wall by the vascular coupling device.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

The invention claimed is:

1. A coupling device for providing a coupling site on a body lumen, the device comprising:
 a back ring configured to fit around the body lumen, the back ring having a rear proximal portion and a forward distal portion; and
 an engaging coupler including
  a body that defines an inner lumen, the inner lumen being sized to at least partially receive the forward distal portion of the back ring,
  a plurality of engaging arms extending distally from the body, and
  a plurality of cuts with radial depth disposed in an outer surface of the engaging coupler,
 wherein the engaging coupler is configured to enable attachment of the coupling device to an identical coupling device, the plurality of cuts of the engaging coupler being configured to accommodate engaging arms of the identical coupling device when the coupling devices are attached, and
 wherein the plurality of cuts are angled so as to urge the engaging arms of the identical coupling device radially outward from the outer surface of the engaging coupler when the coupling devices are attached.

2. The device of claim 1, wherein each of the plurality of cuts is positioned between adjacent engaging arms.

3. The device of claim 1, wherein the plurality of engaging arms are disposed around a circumference of the engaging coupler at substantially equal angular displacements.

4. The device of claim 1, wherein the coupling device has two engaging arms and wherein the engaging arms are circumferentially disposed about 180 degrees from each other.

5. The device of claim 1, wherein the engaging arms each comprise a hook.

6. The device of claim 5, wherein the hook includes an undercut groove.

7. The device of claim 5, wherein the back ring includes a groove on a rear face of the back ring, and wherein the hook is configured to engage with the groove on the rear face of the back ring.

8. The device of claim 1, wherein the engaging coupler further comprises a plurality of proximal engaging arms extending proximally from the body of the engaging coupler.

9. The device of claim 8, wherein the proximal engaging arms extend proximally beyond the back ring to engage with a rear face of the back ring to limit proximal movement of the back ring relative to the engaging coupler.

10. The device of claim 1, wherein the coupling device comprises a bio-absorbable material.

11. The device of claim 1, wherein the engaging coupler has an elliptically-shaped outer surface.

12. The device of claim 11, wherein the elliptically-shaped outer surface includes a major axis and a minor axis, the engaging arms being disposed at the major axis and the cuts being disposed at the minor axis.

13. A vascular coupling system for coupling a first vessel end to a second vessel end, the system comprising:
 a first coupling device configured for attachment to the first vessel end; and
 a second coupling device configured for attachment to the second vessel end, the first and second coupling devices being configured to couple to each other to thereby connect the first vessel end and the second vessel end, the first and second coupling devices each including
  a back ring configured to fit around a respective vessel near the respective vessel end, the back ring having a distal portion, proximal portion, and a rear face located at a proximal end, and
  an engaging coupler with a body that defines a lumen sized to at least partially receive the distal portion of the back ring, the engaging coupler including a plurality of engaging arms extending distally from the body and including a plurality of cuts in an outer surface of the engaging coupler,
 wherein the first and second coupling devices are configured such that when coupled together, the engaging arms of the first coupling device extend through the cuts of the engaging coupler of the second coupling device, and the engaging arms of the second coupling device extend through the cuts of the engaging coupler of the first coupling device, and
 wherein the first and second coupling devices are configured such that when coupled together, the engaging arms of the first coupling device extend beyond the back ring of the second coupling device to engage with the rear face of the back ring of the second coupling device, and the engaging arms of the second coupling device extend beyond the back ring of the first coupling device to engage with the rear face of the back ring of the first coupling device.

14. The system of claim 13, wherein the engaging arms of the first and second coupling devices are equally spaced around outer surfaces of their respective engaging couplers.

15. The system of claim 13, wherein the first and second coupling devices are identical.

16. A method for coupling a first vessel end to a second vessel end, the method comprising:
 providing the vascular coupling system of claim 14;
 positioning the back ring of the first coupling device circumferentially around the first vessel end;
 everting the first vessel end over an outer diameter of the back ring of the first coupling device;
 assembling the first coupling device by positioning the engaging coupler of the first coupling device over the first vessel end and over an outer surface of the back ring of the first coupling device, creating a friction fit of the engaging coupler of the first coupling device and the back ring of the first coupling device with the first vessel end disposed therebetween;
 assembling the second coupling device on the second vessel end; and
 engaging the first coupling device with the second coupling device.

17. A coupling device for providing a coupling site on a body lumen, the device comprising:
 a back ring configured to fit around the body lumen, the back ring having a rear proximal portion and a forward distal portion; and
 an engaging coupler including
  a body that defines an inner lumen, the inner lumen being sized to at least partially receive the forward distal portion of the back ring, a plurality of engaging arms extending distally from the body, and a plurality of cuts with radial depth disposed in an outer surface of the engaging coupler, wherein the engaging coupler is configured to enable attachment of the coupling device to an identical coupling device, the plurality of cuts of the engaging coupler being configured to accommodate engaging arms of the identical coupling device when the coupling devices are attached, wherein the engaging coupler further comprises a plurality of proximal engaging arms extending proximally from the body of the engaging coupler, and wherein the proximal engaging arms extend proximally beyond the back ring to engage with a rear face of the back ring to limit proximal movement of the back ring relative to the engaging coupler.

18. A method for coupling a first vessel end to a second vessel end, the method comprising:

(i) providing a vascular coupling system for coupling the first vessel end to the second vessel end, the system comprising:

a first coupling device configured for attachment to the first vessel end; and a second coupling device configured for attachment to the second vessel end, the first and second coupling devices being configured to couple to each other to thereby connect the first vessel end and the second vessel end, the first and second coupling devices each including a back ring configured to fit around a respective vessel near the respective vessel end, the back ring having a distal portion, proximal portion, and a rear face located at a proximal end, and an engaging coupler with a body that defines a lumen sized to at least partially receive the distal portion of the back ring, the engaging coupler including a plurality of engaging arms extending distally from the body and including a plurality of cuts in an outer surface of the engaging coupler, wherein the first and second coupling devices are configured such that when coupled together, the engaging arms of the first coupling device extend through the cuts of the engaging coupler of the second coupling device, and the engaging arms of the second coupling device extend through the cuts of the engaging coupler of the first coupling device;

(ii) positioning the back ring of the first coupling device circumferentially around the first vessel end;

(iii) creating cuts in a portion of the first vessel end and extending the first vessel end beyond a front edge of the back ring of the first coupling device;

(iv) everting the first vessel end over an outer diameter of the back ring of the first coupling device;

(v) assembling the first coupling device by positioning the engaging coupler of the first coupling device over the first vessel end and over an outer surface of the back ring of the first coupling device, creating a friction fit of the engaging coupler of the first coupling device and the back ring of the first coupling device with the first vessel end disposed therebetween;

(vi) assembling the second coupling device on the second vessel end; and (vii) engaging the first coupling device with the second coupling device.

* * * * *